United States Patent [19]

Sankaram et al.

[11] Patent Number: 5,993,850
[45] Date of Patent: Nov. 30, 1999

[54] PREPARATION OF MULTIVESICULAR LIPOSOMES FOR CONTROLLED RELEASE OF ENCAPSULATED BIOLOGICALLY ACTIVE SUBSTANCES

[75] Inventors: Mantripragada B. Sankaram, San Diego; Sinil Kim, Solana Beach, both of Calif.

[73] Assignee: SkyePharma Inc., San Diego, Calif.

[21] Appl. No.: 08/305,158

[22] Filed: Sep. 13, 1994

[51] Int. Cl.[6] ................................................. A61K 9/127
[52] U.S. Cl. .......................... 424/450; 264/4.1; 264/4.3; 424/417; 436/829
[58] Field of Search .................................. 424/450, 1.21, 424/9.321, 9.51, 417; 436/829; 935/54; 428/402.2; 264/4.1, 4.3, 4.6

[56] References Cited

U.S. PATENT DOCUMENTS

| | | |
|---|---|---|
| 4,078,052 | 3/1978 | Papahadjopoulos . |
| 4,089,801 | 5/1978 | Schneider . |
| 4,145,410 | 3/1979 | Sears . |
| 4,224,179 | 9/1980 | Schneider . |
| 4,235,871 | 11/1980 | Papahadjopoulos et al. . |
| 4,310,506 | 1/1982 | Baldeschwieler et al. . |
| 4,394,372 | 7/1983 | Taylor . |
| 4,522,803 | 6/1985 | Lenk et al. . |
| 4,588,578 | 5/1986 | Fountain et al. . |
| 4,599,227 | 7/1986 | Dees et al. . |
| 4,610,968 | 9/1986 | Fountain et al. . |
| 4,752,425 | 6/1988 | Martin et al. . |
| 4,769,250 | 9/1988 | Forssen . |
| 4,781,871 | 11/1988 | West, III et al. . |
| 4,920,016 | 4/1990 | Allen et al. . |
| 5,000,959 | 3/1991 | Iga et al. . |
| 5,021,200 | 6/1991 | Vanlerberghe et al. . |
| 5,077,056 | 12/1991 | Bally et al. . |
| 5,094,854 | 3/1992 | Ogawa et al. ........................... 424/423 |
| 5,204,112 | 4/1993 | Hope et al. . |
| 5,211,955 | 5/1993 | Legros et al. . |
| 5,422,120 | 6/1995 | Kim ...................................... 424/450 |
| 5,576,017 | 11/1996 | Kim ...................................... 424/450 |
| 5,766,627 | 6/1998 | Sankaram ............................... 424/450 |

FOREIGN PATENT DOCUMENTS

| | | |
|---|---|---|
| 2050287 | 1/1981 | United Kingdom . |

OTHER PUBLICATIONS

Heath, PNAS 80 p 1377–1381, Mar. 1983.

An Extended–Release Formulation of Methotrexate For Subcutaneous . . . Bonetti, et al., *Cancer Chemotherapy and Pharmacology.*, In Press, 1994.

Novel Multilayered Lipid Vesicles: Comparison of Physical Characteristics of Multilamellar Liposomes and Stable Plurilamellar Vesicles Grunor, et al., *Biochemistry*, No. 12, 24:2833–2842, Jun. 4, 1985.

Quantitative Cerebrospinal Fluid Cytology in Patients Receiving Intracavitary Chemotherapy Russack, et al., *Ann. Neurol.*, 34:108–112, 1993.

Extended Cerebrospinal–Fluid Cytarabine Exposure Following Intrathecal Administration of DTC 101 Kim, et al., *J. Clin. Oncol.*, 11: 2186–2193, 1993.

Liposomes as Carriers of Cancer Chemotherapy: A Review Kim, *Drugs*, No. 4, 46:618–638, 1993.

Extended–Release Formulation of Morphine for Subcutaneous Administration Kim, et al., *Cancer Chemother. Pharmacol.*, 33:187–190, 1993.

Production and Size Control of Large Unilamollar Liposomes by Emulsification Ishii, *Liposome Technology*, 1:111–121, 1993.

Structural Properties and Functional Roles of Phospholipids In . . . Cullis, et al., *Phospholipids and Cellular Regulation*, 1:65–123, 1985.

Modulation of the Peritoneal Clearance of Liposomal Cytosine Arabinoside by . . . Kim, et al., *Cancer Chemother. Pharmacology*, 19:307–310, 1987.

Multivesicular Liposomes Containing Bleomycin for Subcutaneous Administration Roy, et al., *Cancer Chemother. Pharmacology*, 28:105–108, 1991.

Prolongation of Drug Exposure in Cerebrospinal Fluid by Encapsulation Into . . . Kim, et al., *Cancer Research*, 55:1596–1598, Apr. 1, 1993.

Direct Cerebrospinal Fluid Delivery of an Antiretroviral Agent Using . . . Kim, et al., *Jrnl. of Infectious Diseases.*, 162:750–752, 1990.

Treatment of Leptomeningeal Metastasis with Intraventricular Administration of . . . Chamberlain, et al., *Archives of Neurol*, No. 3, 50: 261–264, 1993.

A Slow–Release Methotrexate Formulation for Inrathecal Chemotherapy Chatelut, et al., *Cancer Chemother. Pharmacol.*, 32:179–182, 1993.

Preparation of Cell–Size Unilamellar Liposomes with High Captured Volume and Defined Size . . . Kim, et al., *Biochim. Biophys. Acta*, 646:1–9, 1981.

Preparation of Multivesicular Liposomes Kim, et al., *Biochim. Biophys. Acta*, 728:339–348, 1983.

Preparation of Multilamellar Vesicles of Defined Size–Distribution by Solvent–Spherule . . . Kim, et al., *Biochim. Biophys. Acta*, 812:793–801, 1985.

Multivesicular Liposomes Containing Cytarbine Entrapped in the Presence of . . . Kim, et al., *Cancer Treat. Rep.*, 71:705–711, 1987.

(List continued on next page.)

*Primary Examiner*—Gollamudi S. Kishore
*Attorney, Agent, or Firm*—Fish & Richardson P.C.

[57] ABSTRACT

Disclosed are multivesicular liposomes (MVL's) containing biologically active substances, the multivesicular liposomes having defined size distribution, adjustable average size, adjustable internal chamber size and number, and a controlled and variable release rate of the biologically active substance. The process involves encapsulating at least one biologically active substance and optionally an osmotic spacer in a first aqueous component encapsulated within the liposomes. The rate of release of the active substance into the surrounding environment in which the liposomes are introduced can be decreased by increasing the osmolarity of the first aqueous component or increased by decreasing the osmolarity.

42 Claims, No Drawings

OTHER PUBLICATIONS

Multivesicular Liposomes Containing Cytosine 1-β-D-Arabinofuranosylcytosine for Slow-Release Intrathecal Therapy Kim, et al., *Cancer Research*, 47:3935–3937, 1987.

Multivesicular Liposomes Containing Cytosine for Slow Release . . . Kim, et al., *Cancer Treat Rep.*, 71:447–450, 1987.

Tobramycin Liposomes. Single Subconjunctival Therapy of . . . Assil, et al., *Investigative Ophthalmology and Visual Science*, No. 13, 32:3216–3220, Dec. 1991.

Liposome Suppression of Proliferative Vitreorctinopathy. Rabbit . . . Assil, et al., *Investigative Ophthalmology and Visual Science*, No. 11, 32:2891–2897, Oct. 1991.

Magnetic Resonance Imaging of Rabbit Brain After Intra-carotid Injection . . . Turski, et al., *Magnetic Resonance in Medicine*, No. 2, 7:184–196, Jun. 1988.

Filtering Surgery in Owl Monkeys Treated With the Antimetabolite . . . Skuta, et al., *American Journal of Ophthalmology*, No. 5, 103:714–716, May 15, 1987.

Multivesicular Liposomes. Sustained Release of the Antimotabolite . . . Assil, et al., *Archives of Ophthalmology*, No. 3, 105: 400–403, Mar. 1987.

Weak Acid–Induced Release of Liposome–Encapsulated Carboxyfluorescein Barbet, et al., *Biochimica et Biophysica Acta*, No. 3, 772:347–356, May 30, 1984.

Studies on Phosphatidylcholine Vesicles Formation and Physical Characteristics Huang, *Biochemistry*, 8:334–352, 1969.

Diffusion of Univalent Ions Across The Lamellae of Swollen Phospholipids Bangham, *J. Mol. Bio.*, 13:238–252, 1965.

Comparative Properties and Methods of Preparation of Lipid Vesicles (Liposomes) Szoka, et al., *Ann. Rev. Biophys. Bioengineering*, 9:467–508, 1980.

Evaluation of Retinal Toxicity and Liposome Encapsulation of the Anti–CMV Drug 2'–nor–cyclic GMP Shakiba, et al., *Investigative Ophthalmology and Visual Science*, No. 10, 34:2903–2910, Sep. 1993.

Fibrin–Enmeshed Tobramycin Liposomes: Single Application Topical Therapy of . . . Frucht–Perry, et al., *Cornea*, No. 5, 11:393–397, Sep. 1992.

PREPARATION OF MULTIVESICULAR LIPOSOMES FOR CONTROLLED RELEASE OF ENCAPSULATED BIOLOGICALLY ACTIVE SUBSTANCES

BACKGROUND OF THE INVENTION

1. Field of the Invention

The present invention relates to a multivesicular liposome composition of liposomes encapsulating biologically active substances. More particularly, the present invention relates to methods to produce and use multivesicular liposomes with controllable release rate of the encapsulated substance.

2. Description of Related Art

Optimal treatment with many drugs often requires that the drug level be maintained for a prolonged period of time. For example, optimal anti-cancer treatment with cell cycle-specific antimetabolites requires maintenance of a cytotoxic drug level for a prolonged period of time. Cytarabine is a highly schedule-dependent anti-cancer drug. Because this drug kills cells only when they are synthesizing DNA, prolonged exposure at therapeutic concentration of the drug is required for optimal cell kill. The therapeutic effectiveness of such agents is often further complicated by the fact that the half-life after an intravenous or subcutaneous dose may be as short as a few hours. To achieve optimal cancer cell kill with a cell cycle phase-specific drug like cytarabine, there are two major requirements: first, the cancer cell must be exposed to a high concentration of the drug without doing irreversible significant harm to the host; and second, the tumor must be exposed to the drug for a prolonged period of time to maximize the number of cancer cells which are in the susceptible DNA synthesis cycle of cell proliferation.

An example of another class of drugs that are schedule-dependent is the aminoglycoside class of antibiotics. For instance, amikacin is an aminoglycoside antibiotic which has clinically significant activity against strains of both gram negative and gram positive bacteria. Under existing therapeutic procedures, the drug is normally administered by intravenous or intramuscular routes on a once or twice a day schedule. The most commonly used clinical dose is 15 mg/Kg/day which is equivalent to a maximum recommended daily dose of 1 g per day. However, this approach results in systemic exposure to the patients, and depending on the drug, increases risk of toxic side effects. Consequently, a local depot slow-release preparation for treatment of infections such as those confined to a local region of soft tissue or bone would be advantageous in increasing local tissue levels of the drug, compared with therapeutic systemic doses, while reducing or avoiding the systemic toxicity of the free drug.

Especially useful would be controlled release preparations that can be used to deliver therapeutic levels of drugs over periods ranging from hours, days, or even weeks.

One approach which has been used to provide controlled release compositions for drug delivery is liposome encapsulation. Among the main types of liposomes, multivesicular liposomes (Kim, et al., *Biochim. Biophys. Acta;* 728:339–348, 1983), are uniquely different from unilamellar liposomes (Huang, *Biochemistry;* 8:334–352, 1969; Kim, et al., *Biochim. Biophys. Acta;* 646:1–10, 1981), multilamellar liposomes (Bangham, et al., *J. Mol. Bio.,* 13:238–252, 1965), and stable plurilamellar liposomes (U.S. Pat. No. 4,522,803). In contrast to unilamellar liposomes, multivesicular liposomes contain multiple aqueous chambers. In contrast to multilamellar liposomes, the multiple aqueous chambers of multivesicular liposomes are non-concentric.

The prior art describes a number of techniques for producing various types of unilamellar and multilamellar liposomes; for example, U.S. Pat. No. 4,522,803 to Lenk; U.S. Pat. No. 4,310,506 to Baldeschwieler; U.S. Pat. No. 4,235,871 to Papahadjopoulos; U.S. Pat. No. 4,224,179 to Schneider; U.S. Pat. No. 4,078,052 to Papahadjopoulos; U.S. Pat. No. 4,394,372 to Taylor; U.S. Pat. No. 4,308,166 to Marchetti; U.S. Pat. No. 4,485,054 to Mezei; and U.S. Pat. No. 4,508,703 to Redziniak; Szoka, et al., 1980, *Ann. Rev. Biophys. Bioeng.,* 9:465–508; *Liposomes,* Marc J. Ostro, Ed., Marcel-Dekker, Inc., New York, 1983, Chapter 1; Poznansky and Juliano, *Pharmacol. Rev.,* 36:277–236, 1984. The prior art also describes methods for producing multivesicular liposomes (Kim, et al., *Biochim. Biophys. Acta,* 728:339–348, 1983).

In the method of Kim, et al., (*Biochim. Biophys. Acta,* 728:339–348, 1983) the encapsulation efficiency of some small molecules such as cytosine arabinoside, also known as cytarabine or Ara-C, was relatively low, and the release rate of encapsulated molecules in biological fluids was high. Subsequently, a composition was developed which used hydrochloride to slow the release rate of encapsulated molecules in biological fluids (U.S. Patent continuation-in-part application of application Ser. No. 08/020,483, filed Feb. 21, 1993, by Kim).

Further research has shown that the release rate of substances from multivesicular liposomes in human plasma can be controlled by means of varying the nature of the acid solution in which the substance is dissolved prior to forming the multivesicular liposome (U.S. patent application Ser. No. 08/153,657, filed Nov. 16, 1993, Sankaram and Kim). In these studies, certain mineral acids such as hydrochloric, nitric and perchloric acids produced the slowest release rates, whereas other acids, such as acetic, trifluoroacetic, and trichloroacetic resulted in intermediate release rates. The fastest release rates were obtained using di- and tri-protic acids such as sulfuric and phosphoric acids. The composition of liposomes produced by this method has the disadvantage that it requires the use of acid to produce a multivesicular liposome with desirable drug release kinetics. Furthermore, some of the acids which might provide desirable drug release rates from multivesicular liposomes may present pharmaceutical process problems, such as corrosion of metallic containers and parts used in the manufacture. Also, potential problems with the stability of acid-labile substances could be avoided if multivesicular liposomes which are practical in an in vivo environment could be produced without the use of acid.

Studies have shown that the rate of release of the encapsulated biological substance from liposomes into an aqueous environment can be modulated by creating a membrane potential by introducing protonophores or ionophores into liposomes (U.S. Pat. No. 5,077,056). In addition, a method for controlling the release rate of drugs from vesicle compositions is disclosed in European Patent Application EP 0 126 580. In this latter method, a composition was provided comprising a solution of a therapeutic agent encapsulated in vesicles which were suspended in a solution containing sufficient solute to provide a certain osmolarity. This osmolarity was at least substantially isotonic with respect to the osmolarity of the solution within the vesicles which, in turn, had a greater osmolarity than physiological saline. The osmolarity of the solution within the vesicles was held constant, while the osmolarity of the solution in which the vesicles are suspended was varied. Under these conditions, the release rate decreased as the suspending medium approached an isotonic, or even hypertonic relationship with respect to the solution within the vesicles. However, a drawback of this method is that the osmolarity of the medium into which the therapeutic agent is released must be varied in order to control the rate of release. As a consequence, these compositions are severely limited in terms of their practical use, for example, in pharmaceutical applications, since the osmolarity of the biological fluid at the site of administration of the drug delivery system is substantially fixed and cannot be varied. For example, biological fluids such as plasma, are close to isotonic with respect to normal saline (0.9 wt % NaCl in water), which has an osmolarity of 310 mOsm. Therefore, the osmolarity of the suspending medium should ideally be close to 310 mOsm.

In view of the perceived limitations with existing liposome compositions and production methodology, techniques which do not rely upon the use of acids for production of stable multivesicular liposomes are needed. The present invention addresses this need.

SUMMARY OF THE INVENTION

The present invention provides multivesicular liposomes (MVL's) with controlled release of a biologically active substance. The rate of release of the biologically active substance into the physiological environment, such as human tissue in vivo, is controlled by varying the osmolarity of the first aqueous component which is encapsulated within the liposomes. In so doing, the MVL's of the invention achieve greatly improved results by providing a sustained therapeutic release of drug when introduced to an in vivo site. Unexpectedly, as the osmolarity of the first aqueous component which is encapsulated within the liposomes is increased, the rate of release decreases.

Osmolarity of the first aqueous component can be increased either by increasing the concentration of the biologically active substance or by addition of an osmotic spacer.

The present invention also provides non-acidic methods for making multivesicular liposomes with controlled release characteristics which provide for prolonged in vivo therapeutic use. The multivesicular liposomes of the invention have high encapsulation efficiency, controlled release rate of the encapsulated substance, well defined, reproducible size distribution, spherical shape, easily adjustable average size and adjustable internal chamber size and number.

The process of the invention for producing multivesicular lipid vesicles or multivesicular liposomes comprises (a) dissolving in one or more organic solvents a lipid component containing at least one amphipathic lipid and one neutral lipid, (b) mixing the lipid component with an immiscible first aqueous component containing one or more biologically active substances to be encapsulated, (c) forming a water-in-oil emulsion from the two immiscible components, (d) transferring and immersing the water-in-oil emulsion into a second immiscible aqueous component forming solvent spherules, and (e) removing the organic solvents, such as by evaporation, from the solvent spherules. The amphipathic lipid(s) can be selected from amphipathic lipids with a net negative charge; sterols; and zwitterionic lipids. The release rate of encapsulated molecules into biological fluids and in vivo can be decreased either by increasing the concentration of the biologically active substance, by using an osmotic spacer or by combined use of increased substance and osmotic spacer.

DESCRIPTION OF PREFERRED EMBODIMENTS

The present invention is directed to multivesicular liposome (MVL) compositions which allow controlled release of therapeutically active substance in biological fluids. In these compositions the osmolarity of the encapsulated aqueous phase is manipulated in a novel manner to achieve sustained release of the encapsulated therapeutically active substance in the absence of hydrochlorides or acids. By manipulating the process of the invention one of skill in the art can selectively produce MVL's with a broad range of release rates for the substance.

The term "multivesicular liposomes" means man-made, microscopic lipid vesicles enclosing multiple non-concentric aqueous chambers. In contrast, other previously described liposomes such as unilamellar liposomes have a single aqueous chamber and multilamellar and plurilameller liposomes have multiple concentric "onion-skin"-like membranes in between which are spaces containing an aqueous component.

The term "solvent spherule" means a microscopic spheroid droplet of organic solvent, within which are multiple smaller droplets of the aqueous component containing the biologically active agent. The solvent spherules are suspended and totally immersed in a second aqueous component.

The term "neutral lipid" means oil or fats that have no vesicle-forming capability by themselves and lack a charged or hydrophilic "head" group. Examples of neutral lipids include, but are not limited to, glycerol esters, glycol esters, tocopherol esters, sterol esters which lack a charged or hydrophic "head-group", and alkanes and squalene.

The term "amphipathic lipids" means those molecules that have a hydrophilic "head" group and hydrophobic "tail" group and may have membrane-forming capability. As used herein, amphipathic lipids include those amphipathic lipids having a net negative charge, a net positive charge, zwitterionic lipids, and sterols.

The term "zwitterionic lipid" means an amphipathic lipid with a net charge of zero at its isoelectric point.

As used herein, the term "biologically active", when used to describe substances present in the chambers of the multivesicular liposome, includes substances which possess biological activity in the form as presented in the vesicle as well as substances which become active after release from the vesicle chamber (i.e., possess "quiescent" biological activity), such as a pro-drug which is converted upon interaction with an enzyme into an active moiety with therapeutic activity.

In addition, biologically active substances which can be incorporated include substances which act indirectly. Alternatively, such substances may act as an osmotic spacer as described herein. For example, various excipients and stabilizers may be present. Such substances may act, for example, to increase the shelf life or bioavailability of a particular drug. Alternatively, many substances commonly classified as excipients may actually possess direct biological activity from very slight to quite significant. For example, the common excipient mannitol can also act biologically as a diuretic and even water may act biologically to affect dehydration. Such indirectly active substances include aqueous or non-aqueous solutions, suspensions, and emulsions. Examples of non-aqueous solutions are propylene glycol, polyethylene glycol, vegetable oils such as olive oil, and injectable organic esters such as ethyl oleate. Aqueous carriers include water, alcoholic-aqueous solutions, emulsions or suspensions, including saline and buffered media. Parenteral vehicles include sodium chloride solution, Ringer's dextrose, dextrose, and lactated Ringer's solution. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like (see, Remingtons Pharmaceutical Sciences, 16th Ed., A. Oslo, ed., Mack, Easton, Pa. 1980). Those of ordinary skill in the art can readily ascertain and envision various combinations of compounds which can be utilized in the vesicles of the invention without resorting to undue experimentation.

Osmolarity is defined as the sum of molar concentrations of solutes present in an aqueous solution. If the solute is present in a dissociated, ionized or aggregated form, osmolarity is defined as the sum of the molar concentrations of the dissociated, ionized or aggregated forms. The solutes include, but are not limited to, biologically active agents and osmotic spacers.

The term "osmotic spacer" means any biologically compatible solute molecule, in an aqueous solution, that is not the biologically active substance. Both electrolytes and non-electrolytes function as osmotic spacers. In determining whether any particular molecule will function as an osmotic spacer or in determining the concentration of osmotic spacer encapsulated within a multivesicular liposome, consideration must be given to whether, under conditions within the multivesicular liposome (for example, pH), the molecule is wholly or partially ionized and whether such ions will permeate the lipid membrane (The Bimolecular Lipid Bilayer Membrane, Mahendra K. Jain, van Nostrand Reinhold Co., 1972, 470 pp.). One skilled in the art will appreciate that for use in the present invention, the osmotic spacer must be selected so as to avoid substances that would prove toxic or otherwise harmful to a subject undergoing therapy by use of the MVL of this invention. Those of skill in the art can readily evaluate the suitability of a given osmotic spacer for use in the present invention without resort to undue experimentation.

The term "first aqueous component" means the aqueous phase containing the biologically active substance, optionally in the presence of an osmotic spacer, used in the process to prepare multivesicular liposomes.

The term "osmolarity of the first aqueous component" means the osmolarity of the aqueous component containing the biologically active substance used in the process to prepare multivesicular liposomes.

The term "physiologically relevant aqueous environment" means biological fluids such as plasma, serum, cerebrospinal, intramuscular, subcutaneous, peritoneal, intraocular, or, synovial fluids, and storage media such as 0.9 wt % saline or buffered saline that are nearly isotonic with respect to the biological fluids.

The prior art methods of controlling the rate of release of the encapsulated biological substance into the aqueous environment rely on 1.) the nature of the acid solution within the liposomes, or 2.) increasing the osmolarity of the external aqueous environment into which the liposomes are introduced with respect to the osmolarity of the aqueous component within the liposomes. The logical corollary of the latter method is that the rate of release of the encapsulated substance should increase as the osmolarity of the first aqueous component is increased while keeping constant the osmolarity of the aqueous medium into which the liposomes are to be introduced. However, the findings of the present invention surprisingly are the opposite of what is expected based on the prior art teachings, namely, that the rate of release of the encapsulated substance actually decreases as the osmolarity of the internal aqueous component within the MVL's increases even though the osmolarity of the external aqueous medium remains constant. Accordingly, the method of this invention uses osmolarity of the first aqueous component, which is encapsulated within the multivesicular liposomes, to control release where the osmotic strength of the external medium is near physiological.

In addition, when MVL's are produced which include an osmotic spacer, at a given concentration of the biologically active substance, increasing the concentration of osmotic spacer will unexpectedly decrease the release rate of the substance. The decrease in release rate with increase in osmolarity of the first aqueous component enhances the utility of the multivesicular liposomes for any type of therapeutic treatment that benefits from prolonged release of the therapeutic agent.

To decrease the release rate of encapsulated therapeutic or other active agents from the multivesicular liposomes of the invention, the osmolarity of the first aqueous component within the MVL's is increased relative to that of the physiologically relevant aqueous environment in which the MVL's are stored (such as 0.9 wt % saline) or into which the MVL's are introduced (both in vitro and in vivo) either by increasing the concentration of the active substance or by use of an osmotic spacer. Conversely, the release rate can be increased either by decreasing the concentration of the active substance, or by decreasing the concentration of, or eliminating the use of, an osmotic spacer. The osmolarity of the first aqueous component can also be hypertonic with respect to the physiologically relevant aqueous environment to provide an optimum decrease in the rate of release of the biologically active substance from the liposomes accompanied by a greater yield for the process of encapsulation than under isotonic conditions. Therefore, it is contemplated within the scope of this invention that the first aqueous component can be hypotonic, isotonic or hypertonic with respect to the storage medium or the aqueous environment into which the biologically active agent is to be released. Consequently, one of skill in the art can routinely produce an MVL with a pre-selected rate of release of the biologically active substance which is optimal for a given therapy.

Since the osmolarity of normal saline is similar to that of human plasma and other in vivo environments, such as cerebrospinal fluid, synovial fluid, as well as subcutaneous and intramuscular spaces, saline can be used as a predictive model of MVL drug release in such environments. The preferred use of the MVL's of the invention is for in vivo injection or implantation into tissue or body cavities (for instance, as drug depots) and they are preferably stored in a medium such as normal saline, phosphate-buffered saline, or other osmotically similar medium.

Briefly, in the method embraced by the present invention MVL's are produced by first forming a water-in-oil emulsion made by dissolving the amphipathic lipid(s) and the neutral lipid in a volatile organic solvent for the lipid component, adding to the lipid component an immiscible first aqueous component containing a biologically active substance to be encapsulated and then emulsifying the mixture, for example, through turbulence created by mixing, shaking, sonication, by ultrasonic energy, nozzle atomization, or by combinations thereof. The entire emulsion is then immersed in a second aqueous component and then agitated mechanically, as above, to form solvent spherules suspended in the second aqueous component. The resulting solvent spherules are made up of multiple aqueous droplets in which the biologically active substance is contained (a water-in-oil-in-water double emulsion).

The volatile organic solvent is removed from the spherules, for example, by passing a stream of gas over or through the suspension to evaporate the solvent. When the solvent is completely evaporated, multivesicular liposomes are formed. Representative gases satisfactory for use in evaporating the solvent include nitrogen, helium, argon, oxygen, hydrogen and carbon dioxide. Alternatively the organic solvent can be removed by solvent removal systems commonly employed such as sparging with the above gases, evaporation under reduced pressure, and spray drying.

Osmotic spacers, which include, but are not limited to, glucose, sucrose, trehalose, succinate, cyclodextrin, arginine, galactose, mannose, maltose, mannitol, glycine, lysine, citrate, sorbitol, dextran, and combinations thereof, may be used to form multivesicular liposomes and to control the release rate of the encapsulated substance from multivesicular liposomes. The concentration of the encapsulated biologically active substance can vary from about a few picomoles to about several hundred millimoles. The concentration of biologically active substance will vary depending upon such characteristics as the disease to be treated, age and condition of the patient, as well as the particular properties of the substance. In the case where the substance is normally associated with side effects such as toxicity it might be desirable to produce an MVL with a lower concentration of substance and utilize a higher concentration of osmotic spacer. The interrelationship of these various parameters can be easily evaluated by one of skill in the art in selecting and producing a given MVL composition without resort to undue experimentation.

Many different types of volatile hydrophobic solvents such as ethers, hydrocarbons, halogenated hydrocarbons, supercritical fluids including but not limited to $CO_2$, $NH_3$, and freons may be used as the lipid-phase solvent. For example, diethyl ether, isopropyl and other ethers, dichloromethane, chloroform, tetrahydrofuran, halogenated ethers, esters and combinations thereof are satisfactory.

Various types of lipids can be used to make the multivesicular liposomes as long as at least one neutral lipid and at least one amphipathic lipid are included. The amphipathic lipid(s) can be selected from the group consisting of (1) amphipathic lipids with a net negative charge; (2) sterols; and (3) zwitterionic lipids. For instance, the lipid component can comprise a neutral lipid and an amphipathic lipid with a net negative charge. In an alterative embodiment, the lipid component further comprises a sterol. And in yet another alternative embodiment, the lipid further comprises both a sterol and a zwitterionic lipid.

Examples of zwitterionic lipids are phosphatidylcholines, phosphatidylethanolamines, sphingomyelins, and combinations thereof. Examples of neutral lipids are triglycerides such as triolein, tricaprylin, vegetable oils such as soybean oil, lard, beef fat, tocopherol, squalene and combinations thereof. Examples of amphipathic lipids with net negative charge are cardiolipins, phosphatidylserines, phosphatidylglycerols, phosphatidylinositols, and phosphatidic acids. Examples of amphipathic lipids with a net positive charge are diacyl trimethylammonium propanes, diacyl dimethylammonium propanes and stearylamine.

Various biologically active substances can be incorporated by encapsulation within the multivesicular liposomes. These substances include drugs, as well as other kinds of pharmaceutical materials such as DNA, RNA, proteins of various types, protein hormones such as insulin, growth factors, cytokines, monokines, lymphokines, and proteins and carbohydrates that serve as immunogens for vaccination.

Biologically active substances effective for cosmetic uses can also be incorporated by encapsulation into multivesicular liposomes. These include moisturizers, vitamins, enzymes, and perfumes. In addition, herbicides, pesticides, fungicides etc. are examples of biologically active substances with agricultural uses that can be encapsulated into multivesicular liposomes.

Table 1 includes representative classes of biologically active substances that can be encapsulated in the multivesicular liposomes of this invention.

TABLE 1

| Antianginas | Antiarrhythmics | Antiasthmas |
|---|---|---|
| Antibiotics | Antidiabetics | Antifungais |
| Antihistamines | Antihypertensives | Antiparasitics |
| Antineoplastics | Antivirals | Cardiac Glycosides |
| Herbicides | Hormones | Immunomodulators |
| Monoclonal Antibodies | Neurotransmitters | Nucleic Acids and Analogs |
| Pesticides | Proteins and Glycoproteins | Radio Contrast Agents |
| Radionucleids | Sedatives and Analgesics | Steroids |
| Tranquilizers | Vaccines | Vasopressors |
| Perfumes | Cosmetics | Moisturizers |
| | | Fungicides |

The dosage range appropriate for in vivo use in humans of the biologically active substance in multivesicular liposomes of this invention includes the range of 0.001–6,000 $mg/m^2$ of body surface area. While doses outside the foregoing dose range may be given, this range encompasses the breadth of use for practically all the biologically active substances. However, for a particular therapeutic agent the preferred concentration can be easily ascertained as previously described.

The multivesicular liposomes may be administered by any desired route; for example, intratumoral, intra-articular (into joints), intramuscular, intrathecal, intraperitoneal, subcutaneous, intravenous, intralymphatic, oral and submucosal. The multivesicular liposomes may be modified using methods well known in the art by attaching thereto, either directly, or indirectly, such as by means of a spacer molecule or peptide, target-specific ligands, such as antibodies and other receptor specific protein ligands, in order to impart organ or cell target specificity (Malone, et al., Proc. Nat'l. Acad. Sci, U.S.A., 86:6077, 1989; Gregoriadis, Immunology Today, 11(3):89, 1990; both incorporated by reference).

The following examples illustrate the manner in which the invention can be practiced. It is understood, however, that the examples are for the purpose of illustration and the invention is not to be regarded as limited to any of the specific materials or conditions therein.

EXAMPLE 1

A. Preparation of Multivesicular Liposomes

Step 1) In a clean glass cylinder (2.5 cm inner diameter× 10.0 cm height), were placed 5 mL of a solution containing in chloroform 46.5 ;moles of dioleoyl phosphatidylcholine (Avanti Polar Uipids, Birmingham, Ala.), 10.5 $\mu$moles of dipalmitoyl phosphatidylglycerol (Avanti Polar Uipids, Birmingham, Ala.), 75 $\mu$moles of cholesterol (Sigma Chemical Co., St. Louis, Mo.), 9.0 $\mu$moles of triolein (Avanti Polar Lipids, Birmingham, Ala.). This solution is referred to as the lipid component.

Step 2) Five mL of either first aqueous component, cytarabine (Upjohn, Kalamazoo, Mich.), or amikacin sulfate (Bristol Myers Squibb, Syracuse, N.Y.) dissolved in water, were added into the above glass cylinder containing the lipid component. For cytarabine, the concentrations used were 41 mM, 82 mM, 164 mM, 246 mM, 369 mM, and 410 mM. For amikacin sulfate, the concentrations used were 13 mM, 26 mM, 52 mM, and 88 mM. Amikacin sulfate contains 1.8 sulfate ions per amikacin molecule. Thus, the concentration is multiplied by 2.8 to obtain the osmolarity.

Step 3) For making the water-in-oil emulsion, the mixture of step 2 was stirred with an homogenizer (AutoHomoMixer, Model M, Tokushu Kika, Osaka, Japan) for 8 minutes at a speed of 9000 rpm.

Step 4) For making the chloroform spherules suspended in water, 20 mL of a solution containing 4 percent dextrose and 40 mM lysine was layered on top of the water-in-oil emulsion, and then mixed for 60 seconds at a speed of 4000 rpm to form the chloroform spherules.

Step 5) To obtain the multivesicular liposomes, the chloroform spherule suspension in the glass cylinder was poured into a 1000 mL Erlenmeyer flask containing 30 mL of water, glucose (3.5 g/100 mL), and free-base lysine (40 mM). A stream of nitrogen gas at 7L/minute was passed over the suspension in the flask to slowly evaporate chloroform over 20 minutes at 37° C. Sixty mL of normal saline (0.9% sodium chloride) was added to the flask. The liposomes were then isolated by centrifugation at 600×g for 10 minutes, the supernatant was decanted, and the pellet was resuspended in 50 mL of normal saline. The liposomes were isolated by centrifugation at 600×g for 10 minutes. The supernatant was decanted, and the pellet was resuspended in saline.

B. Determination of Mean Diameter of Multivesicular Liposomes

The mean diameter of multivesicular liposomes prepared as described above was determined by the method of laser light diffraction using the model LA-500 Particle Size Analyzer from Horiba, Inc. (Irvine, Calif.). The mean diameter of the resulting liposomes was in the range from 5 to 20 μm.

C. Plasma Release Assay for Cytarabine

This example demonstrates that the rate of release of cytarabine and amikacin in human plasma at 37° C. decreases with increasing concentration of the drug in the first aqueous component.

Five hundred μL of the multivesicular liposome suspension containing cytarabine was added to 1.2 mL of type O, screened human plasma. The mixture was incubated at 37° C. At desired time intervals, an aliquot was taken, the multivesicular liposomes were isolated as a pellet by centrifugation at 600×g, the pellet was solubilized in isopropyl alcohol, and the amount of cytarabine in the pellet fraction was assayed by high pressure liquid chromatography (e.g. U.S. Pharmacopeia, XXII, p.376, 1990).

D. Plasma Release Assay for Amikacin

Five hundred μL of the multivesicular liposome suspension containing amikacin were added to 1.2 mL of type O, screened human plasma. The mixture was incubated at 37° C. and at desired time intervals an aliquot was taken. The multivesicular liposomes were isolated as a pellet by centrifugation at 600×g. The pellet was solubilized in isopropyl alcohol and the amount of amikacin in the pellet fraction was assayed by a polystyrene bead based fluorescence immunoassay (Varma-Nelson, et al, *Therapeutic Drug Monitoring*, 13:260–262, 1991). The percent retained amikacin was calculated from the amounts obtained by this procedure.

As can be seen in Table 2 encapsulation yield, expressed as a percentage of total drug used in the first aqueous component at different initial concentrations or osmolarities, had a marked influence on the rate of their release from the multivesicular liposomes incubated in human plasma, which is shown as half-life. The half-life of drug release was calculated assuming a simple-exponential decay model. The data in Table 2 is the mean and standard deviation from three experiments. The half-life for release of cytarabine into human plasma remains essentially unchanged under hypertonic conditions relative to the isotonic condition. The data also show that the cytarabine and amikacin half-life values increase with increasing concentration of the biologically active substance (shown as mOsm) encapsulated in the multivesicular liposomes during manufacture up to about 246 mOsm. Increasing the osmolarity of the first aqueous component, which is encapsulated within the multivesicular vesicles unexpectedly results in producing liposomes with enhanced utility for slow release of drugs over long periods of time in human plasma.

TABLE 2

| Drug | Osmolarity (mOsm) | Mean Diameter (μm) | Encapsulation Yield | Half-Life (Days) |
|---|---|---|---|---|
| Cytarabine | 41 | 9.1 ± 0.7 | 18 ± 3 | 1.0 ± 0.3 |
|  | 82 | 10.9 ± 1.1 | 37 ± 2 | 1.8 ± 0.3 |
|  | 164 | 13.3 ± 1.6 | 51 ± 4 | 4.6 ± 1.9 |
|  | 246 | 14.7 ± 1.8 | 61 ± 5 | 14.1 ± 1.5 |
|  | 369 | 16.1 ± 2.4 | 62 ± 3 | 12.1 ± 2.7 |
|  | 410 | 13.4 ± 2.3 | 57 ± 2 | 13.0 ± 3.6 |
| Amikacin sulfate | 36 | 7.0 ± 1.2 | 35 ± 5 | 6.4 ± 2.7 |
|  | 73 | 7.1 ± 1.2 | 42 ± 5 | 23.9 ± 1.4 |
|  | 146 | 7.6 ± 1.1 | 50 ± 6 | 39.6 ± 2.9 |
|  | 246 | 8.3 ± 1.7 | 66 ± 6 | 47.3 ± 4.0 |

EXAMPLE 2

This example demonstrates that the release rate of cytarabine in plasma decreases with increasing osmolarity of the first aqueous component at a fixed concentration of the biologically active substance. Multivesicular liposomes were prepared as described in Step 1 through Step 5 for Example 1, with the following modification for Step 2.

Step 2) Five mL of aqueous component, cytarabine (Upjohn, Kalamazoo, Mich.), dissolved at a concentration of 82 mM either in water, or in 3 wt % glucose, or in 5 wt % glucose, was added into the above glass cylinder containing lipid component. The calculated osmolarities of the resulting solutions are 82, 220 and 335 mOsm, respectively.

The percent of cytarabine retained in multivesicular liposomes after incubation at 37° C. in human plasma for the different glucose concentrations was measured as a function of time of incubation. Table 3 shows the mean diameter, encapsulation yield of cytarabine and the half-life for release in plasma at 37° C. for the compositions containing 0, 3 and 5 wt % glucose. The mean and standard deviation from three experiments is shown in each case. Incorporation of the osmotic spacer, glucose, at different concentrations while the biologically active substance is held at a fixed concentration had a marked influence on the rate of release from the multivesicular liposomes incubated in human plasma. As illustrated by the data in Table 3, the half-life for release of cytarabine from multivesicular liposomes into human plasma increases with increasing osmolarity of the first aqueous component. The encapsulation yield also increases with increasing osmolarity of the first aqueous component up to about 248 mOsm.

TABLE 3

| [Glucose] (wt %) | Osmolarity[a] (mOsm) | Mean Diameter (μm) | Encapsulation Yield | Half-Life (Days) |
|---|---|---|---|---|
| 0 | 82 | 10.9 ± 1.1 | 37 ± 2 | 1.8 ± 0.3 |
| 3 | 248 | 16.5 ± 1.6 | 55 ± 3 | 18.6 ± 5.7 |
| 5 | 359 | 17.9 ± 1.1 | 57 ± 4 | 17.9 ± 4.3 |

[a]Osmolarity includes both cytarabine and glucose.

EXAMPLE 3

This example demonstrates that multivesicular liposomes can be prepared when a normal saline solution is used for the second aqueous component. Multivesicular liposomes were prepared as described below.

Step 1) In a clean glass cylinder (2.5 cm inner diameter× 10.0 cm height), 5 mL of a solution containing 46.5 μmoles of dioleoyl phosphatidylcholine (Avanti Polar Lipids, Birmingham, Ala.), 10.5 μmoles of dipalmitoyl phosphatidylglycerol (Avanti Polar Lipids, Birmingham, Ala.), 75 μmoles of cholesterol (Sigma Chemical Co., St. Louis, Mo.), 9.0 μmoles of triolein (Avanti Polar Lipids, Birmingham, Ala.) in chloroform were placed. This solution is referred to as the standard lipid component.

Step 2) Five mL of first aqueous component, cytarabine (Upjohn, Kalamazoo, Mich.) dissolved in water at a concentration of 246 mM, was added into the above glass cylinder containing the standard lipid component.

Step 3) For making the water-in-oil emulsion, a homogenizer (AutoHomoMixer, Model M, Tokushu Kika, Osaka, Japan) was used by mixing for 8 minutes at a speed of 9000 rpm.

Step 4) For making the chloroform spherules suspended in water, 20 mL of normal saline (0.9% sodium chloride) was layered on top of the water-in-oil emulsion, and then mixed for 60 seconds at a speed of 4000 rpm to form the chloroform spherules. This constitutes the water-in-oil-in-water double emulsion.

Step 5) The chloroform spherule suspension in the glass cylinder was poured into a 1000 mL Erlenmeyer flask containing 30 mL of normal saline (0.9 % sodium chloride). A stream of nitrogen gas at 7L/minute was passed over the suspension in the flask to evaporate chloroform over 20 minutes at 37° C. The liposomes were filtered through a 50 μm filter. The liposomes were isolated from the suspension by centrifugation at 600×g for 10 minutes. The supernatant was decanted, and the pellet was resuspended in saline.

The half-life for release of cytarabine from multivesicular liposomes prepared using a 246 mOsm cytarabine solution in water, and normal saline for the second aqueous component, was 15.7±4.8 days. This value is similar to the half-life for release from multivesicular liposomes prepared by using a 246 mOsm cytarabine solution in water, and a glucose-lysine solution for the second aqueous component (14.1±1.5 days, see Table 2).

EXAMPLE 4

Pharmacokinetic studies in mice were performed to test the slow-release properties of the multivesicular liposomes of the invention in vivo.

Multivesicular liposomes were prepared as described in Example 1. Cytarabine solutions in water at concentrations of 82 mM or 246 mM were used as the first aqueous component. The multivesicular liposomes obtained were washed twice with normal saline, centrifuged at 600×g for 10 minutes, and stored in normal saline at a concentration of 10 mg cytarabine per mL of suspension.

Mice (CD1 ICR, outbred, female) were injected intraperitoneally with multivesicular liposomes containing 2.55±0.25 mg of cytarabine. Before injection, aliquots of the suspension of multivesicular liposomes containing the same amount of cytarabine as intended for injection were taken as time zero samples.

At different time points up to 108 hours after injection, animals were sacrificed by cervical dislocation. Twenty μL of undiluted peritoneal fluid was recovered from the peritoneal cavity into a sample tube containing 200 μL of normal saline. The sample tube was centrifuged in an Eppendorf Microfuge (Brinkman Instruments, Westbury, N.Y.) at maximum speed for 1 minute. The supernatant and pellet were separated. After recovering 20 μL of peritoneal fluid as described above, the peritoneal cavity was washed out thoroughly with 2–3 ml of 0.9% NaCl solution. All samples were stored at −20° C. before analysis.

The pellet and supernatant fractions, and the wash fraction were solubilized with isopropyl alcohol. The amount of cytarabine in the solubilized fractions was assayed by high pressure liquid chromatography (e.g. *U.S. Pharmacopeia*, XXII:376, 1990). The concentrations of cytarabine (μg/mL) in the pellet fraction are given in Table 4. The total amounts of cytarabine (μg) in the intraperitoneal cavity, which are also given in Table 4, were obtained by adding the amounts in the pellet and supernatant fraction of the 20 μL undiluted peritoneal fluid sample, and the amount in the peritoneal wash fraction.

The pharmacokinetic data, i.e. the time-dependent decrease in cytarabine concentrations in the pellet and supernatant fractions and in the total amount, was analyzed with RSTRIP program (MicroMath Scientific Software, Salt Lake City, Utah) using a single compartment model and zero weighting. The decay half-lives are given in Table 4.

A comparison of the data shown in Table 4 with the 82 mM (initial cytarabine concentration) formulation and the 246 mM (initial cytarabine concentration) shows that the total amount of cytarabine decreases more rapidly for the 82 mM formulation than for the 246 mM formulation. The concentration in the pellet fraction also decreases more rapidly for the 82 mM formulation than for the 246 mM formulation. Therefore, this study shows that the rate of release of cytarabine decreases with increasing osmolarity of the first aqueous component, not only in the physiologically relevant environment, namely, human plasma as shown in EXAMPLE 1, but also in vivo.

TABLE 4

Concentration of cytarabine in the pellet fractions
of the peritoneal fluid, and the
total amount of cytarabine in the peritoneal cavity,
at different times subsequent
to intraperitoneal injection of formulations
prepared using a solution containing
either 82 mM cytarabine or 246 mM cytarabine.
A group size of three was used.

| Hours After Intraperitoneal Injection | Concentration in Pellet Fraction ($\mu$g/mL) | | Total Amount ($\mu$g) | |
|---|---|---|---|---|
| | 82 mM Formulation | 246 mM Formulation | 82 mM Formulation | 246 mM Formulation |
| 0 | 9,380 | 9,685 | 2,372 | 2,791 |
| 0.5 | 9,925 ± 371 | 6,896 ± 1,083 | 1,108 ± 67 | 1,202 ± 48 |
| 4 | 1,115 ± 1,108 | 13,360 ± 761 | 150 ± 14 | 1,493 ± 132 |
| 15 | 1,015 ± 922 | 11,493 | 76 ± 58 | 790 ± 419 |
| 64 | ND | 1,493 ± 132 | ND | 388 ± 191 |
| 108 | ND | 634 ± 518 | ND | 58 ± 34 |
| $t^{1/2}(r^2)$ | 1.7(0.974) | 29.6(0.904) | 0.64 (0.989) | 13.6 (0.892) |

ND, not determined;
$t^{1/2}$, Decay Half-Life in Hours.

While presently preferred embodiments of the invention have been given for the purpose of disclosure, changes may be made therein which are within the spirit of the invention as defined by the scope of the appended claims.

We claim:

1. A process for controlling the release of biologically active substances from multivesicillar liposomes comprising the steps of:
    (a) forming a standard first immiscible component by dissolving at least one biologically active substance in a first aqueous solution and then measuring the osmolarity;
    (b) forming a second immiscible component by dissolving at least one amphipathic lipid and at least one neutral lipid in either one or more organic solvents liquid $CO_2$, or liquid $NH_3$, thereby forming a lipid component;
    (c) forming a water-in-oil emulsion by mixing the products of (a) and (b), thereby encapsulating said biologically active substance;
    (d) dispersing the emulsion into a second aqueous component to form spherules;
    (e) removing the organic solvent from the spherules to form multivesicular liposomes;
    (f) measuring the rate of release of the biologically active substance into a physiologically relevant aqueous environment; and
    (g) preparing modified liposomes by repeating steps (a) through (e), except that in (a), the osmolarity of the first aqueous solution is either further increased relative to the standard osmolarity, thereby decreasing the rate of release of the biologically active substance; or further decreased relative to the standard osmolarity, thereby increasing the rate of release of the biologically active substance.

2. The process of claim 1, wherein the amphipathic lipid is an amphipathic lipid with a net negative charge.

3. The process of claim 2, wherein the amphipathic lipid is selected from the group consisting of cardiolipins, phosphatidylserines, phosphatidylglycerols, phosphatidylinositols and phosphatidic acids.

4. The process according to claim 1, wherein the lipid component further comprises a sterol.

5. The process according to claim 4, wherein the lipid component further comprises a zwitterionic lipid.

6. The process according to claim 1, wherein the amphipathic lipid is a zwitterionic lipid.

7. The process according lo claim 6 wherein the zwitterionic lipid is selected from the group consisting of phosphatidylcholines, phosphatidylethanolamines, sphingomyelins, and lysophosphatidylcholines.

8. The process according to claim 1, wherein the amphipathic lipid has a net positive charge.

9. The process according to claim 8, wherein the amphipathic lipid is selected from the group consisting of diacyl trimethylammonium propanes, diacyl dimethylammonium propanes and stearylamine.

10. The process according to claim 1, 2, 4, 6 or 8 wherein the lipid component is selected from the group consisting of a phospholipid and an admixture of phospholipids.

11. The process according to claim 5, wherein the lipid component is selected from the group consisting of a phospholipid and an admixture of phospholipids.

12. The process according to claim 1 or 6, wherein the physiologically relevant aqueous environment is a storage medium.

13. The process according to claim 1 or 6 wherein the physiologically relevant aqueous environment is selected from the group consisting of normal saline, buffered saline, human plasma, serum, cerebrospinal fluid, synovial fluid, intraocular fluid, and intraperitoneal fluid.

14. The process according to claim 1, wherein at least one of the amphipathic lipids has a net negative charge.

15. The process according to claim 1, wherein the amphipathic lipid is provided in admixture with cholesterol.

16. The process according to claim 1, wherein a lipophilic biologically active substance is provided in admixture with the lipid component.

17. The process according to claim 1, wherein the neutral lipid is selected from the group consisting of triglycerides, triolein, tricaprylin, tocopherol, squalene, and combinations thereof.

18. The process according to claim 1, wherein the organic solvent is selected from the group consisting of ethers, hydrocarbons, halogenated hydrocarbons, halogenated ethers, esters, freons, and combinations thereof.

19. The process according to claim 1, wherein the biologically active substance is hydrophilic.

20. The process according to claim 1, wherein the emulsification of the two said components is carried out using a method selected from the group consisting of mechanical agitation, ultrasonic energy, and nozzle atomization.

21. The process according to claim 20, wherein the average size and number of the aqueous chambers within the vesicles are determined by duration of the method of emulsification selected.

22. The process according to claim 1, wherein the aqueous component containing the biologically active substance consists essentially of water and the biologically active substance.

23. The process according to claim 1, wherein the second aqueous component comprises substances selected from the group consisting of lysine, glycine, histidine, glucose, sucrose, trehalose, succinate, cyclodextrin, arginine, galactose, mannose, maltose, mannitol, citrate, sorbitol, dextran, sodium chloride, and combinations thereof.

24. The process according to claim 1, wherein the second aqueous component comprises substances selected from the group consisting of monosaccharides, disaccharides, polysaccharides, and combinations thereof.

25. The process according to claim 1, wherein the removing of the organic solvent is by a solvent removal system selected form the group consisting of sparging, evaporation, passing gas over the solvent spherules, spray drying, and combinations thereof.

26. The process according to claim 1 or 6, wherein the biologically active substance is selected form the therapeutic categories consisting of antianginas, antibiotics, antihistaines, antineoplastics, monoclonal antibodies, radionucleotides, tranquilizers. antiarrhythrnics, antidiabetics, antihypertensives, antiparasitics, cardiac glycosides, immunomodulators, nucleic acids and analogs, radio contrast agents, steroids, vasopressors, vaccines, sedatives and analgesics, and combinations thereof.

27. The process according to claim 1 or 6, wherein the biologically active substance is cytarabine.

28. The process according to claim 1 or 6, wherein the biologically active substance is amikacin.

29. The process according to claim 1 or 6, wherein the biologically active substance is selected from the group consisting of therapeutic proteins and peptides.

30. The process according to claim 1 or 6, wherein the biologically active substance is selected from the group consisting of herbicides, pesticides, fungicides, insecticides, and combinations thereof.

31. The process according to claim 1 or 6, wherein the biologically active substance is a nucleic acid.

32. The process according to claim 1 or 6, wherein the biologically active substance is a cosmetic.

33. The process according to claim 1, wherein the aqueous component comprises sufficient biologically active substance to attain the desired osmolarity.

34. The process according to claim 1, wherein the aqueous component further comprises sufficient osmotic spacer to attain the desired osmolarity.

35. The process according to claim 1, wherein the organic solvent is a volatile hydrophobic solvent.

36. The process according to claim 32, wherein the cosmetic is a perfume, a moisturizer, or a combination thereof.

37. The process according to claim 1 or 6, further comprising attaching a target specific ligand or hydrophilic coating to the multivesicular liposome.

38. The process according to claim 1, wherein the lipid component is step (b) comprises at least one organic solvent, at least one amphipathic lipid and at least one neutral lipid.

39. The process according to claim 8, wherein the lipid component is selected from the group consisting of a phospholipid and an admixture of phospholipids.

40. The process according to claim 35, wherein the volatile hydrophobic solvent is selected from the group consisting of an ether, a hydrocarbons, a halogenated hydrocarbons, and a supercritical fluid.

41. The process according to claim 40, wherein the supercritical fluid is CO2.

42. The process according to claim 1, wherein once the desired osmolarity has been determined, the steps of preparing the standard and measuring the rate of release are no longer performed.

* * * * *

UNITED STATES PATENT AND TRADEMARK OFFICE
CERTIFICATE OF CORRECTION

PATENT NO. : 5,993,850
DATED : NOVEMBER 30, 1999
INVENTOR(S) : MANTRIPRAGADA B. SANKARAM, PH.D. AND SINIL KIM, PH.D.

It is certified that error appears in the above-identified patent and that said Letters Patent is hereby corrected as shown below:

Col. 8, line 56 – ";moles" should read "µmoles"

Col.13, Table 4 – the table should be reformatted as follows:

| Hours After Intraperitoneal Injection | Concentration in Pellet Fraction (µg/mL) | | Total Amount (µg) | |
|---|---|---|---|---|
| | 82 mM Formulation | 246 mM Formulation | 82 mM Formulation | 246 mM Formulation |
| 0 | 9,380 | 9,685 | 2,372 | 2,791 |
| 0.5 | 9,925 ± 371 | 6,896 ± 1,083 | 1,108 ± 67 | 1,202 ± 48 |
| 4 | 1,115 ± 1,108 | 13,360 ± 761 | 150 ± 14 | 1,493 ± 132 |
| 15 | 1,015 ± 922 | 11,493 | 76 ± 58 | 790 ± 419 |
| 64 | ND | 1,493 ± 132 | ND | 388 ± 191 |
| 108 | ND | 634 ± 518 | ND | 58 ± 34 |
| $t^{1/2}$ $(r^2)$ | 1.7 (0.974) | 296. (0.904) | 0.64 (0.989) | 13.6 (0.892) |

ND, not determined; $t^{1/2}$, Decay Half-Life in Hours.

Col. 13, line 46 (Claim 1) – a comma should be placed after "solvents"

Col. 14, line 13 (Claim 7) – "lo" should read "to"

Col. 14, line 13 (Claim 7) – a comma should be placed after "6"

Col. 14, line 23 (Claim 10) – a comma should be placed after "8"

UNITED STATES PATENT AND TRADEMARK OFFICE
CERTIFICATE OF CORRECTION

PATENT NO. : 5,993,850
DATED : NOVEMBER 30, 1999
INVENTOR(S) : MANTRIPRAGADA B. SANKARAM, PH.D. AND SINIL KIM, PH.D.

It is certified that error appears in the above-identified patent and that said Letters Patent is hereby corrected as shown below:

Col. 14, line 32 (Claim 13) – a comma should be placed after "6"

Col. 15, line 11 (Claim 25) – "form" should read "from"

Col. 15, line 15 (Claim 26) – "form" should read "from"

Col. 16, line 19 (Claim 38) – "is" should read "in"

Col. 16, line 19 (Claim 41) – "CO2" should read "$CO_2$"

Signed and Sealed this

Twenty-second Day of May, 2001

Attest:

NICHOLAS P. GODICI

*Attesting Officer*   *Acting Director of the United States Patent and Trademark Office*